United States Patent [19]

Walkowiak et al.

[11] 4,182,829
[45] Jan. 8, 1980

[54] IMPRESSION MATERIALS FOR DENTISTRY

[75] Inventors: Michael Walkowiak, Cologne; Hans-Hermann Schulz, Leichlingen; Hans J. Rosenkranz, Krefeld, all of Fed. Rep. of Germany

[73] Assignee: Bayer Aktiengesellschaft, Leverkusen, Fed. Rep. of Germany

[21] Appl. No.: 904,071

[22] Filed: May 8, 1978

[30] Foreign Application Priority Data

May 28, 1977 [DE] Fed. Rep. of Germany ....... 2724260

[51] Int. Cl.$^2$ ..................... C08G 18/34; C08G 18/67; C08G 18/62
[52] U.S. Cl. ................................. 528/75; 204/159.19; 260/18 TN; 260/37 N; 260/45.8 N; 528/50; 528/52; 528/58; 525/123
[58] Field of Search ............... 260/DIG. 36, 77.5 AP; 528/75

[56] References Cited

U.S. PATENT DOCUMENTS

| | | | |
|---|---|---|---|
| 3,297,745 | 1/1967 | Fekete et al. | 260/471 |
| 3,509,234 | 4/1970 | Burlant et al. | 260/859 |
| 3,553,174 | 1/1971 | Hausslein et al. | 260/77.5 AP |
| 3,641,199 | 2/1972 | Niederhauser et al. | 260/859 R |
| 3,644,569 | 2/1972 | Pietsch et al. | 260/835 |
| 3,709,866 | 1/1973 | Waller | 260/27 R |
| 3,825,518 | 7/1974 | Foster et al. | 260/DIG. 36 |
| 3,862,920 | 1/1975 | Foster et al. | 260/DIG. 36 |
| 3,878,036 | 4/1975 | Chang | 428/424 |
| 3,907,751 | 9/1975 | Knight et al. | 528/75 |

*Primary Examiner*—H. S. Cockeram
*Attorney, Agent, or Firm*—Sprung, Felfe, Horn, Lynch & Kramer

[57] ABSTRACT

The invention provides impression materials for use in dentistry comprising the reaction product of (a) a diisocyanate or triisocyanate, (b) a dihydroxy compound having a molecular weight of from 300 to 10,000 and (c) an unsaturated monohydroxy compound. The invention also includes processes for preparing said impression materials.

11 Claims, No Drawings

IMPRESSION MATERIALS FOR DENTISTRY

The present invention relates to the use of polyurethane resins containing vinyl groups as impression materials, in particular for dentistry.

Impression materials are understood as compositions which pass from a plastic state into a hard or elastic state by means of a hardening process. Impression materials are used in dentistry in order to obtain a congruent reproduction of mucus membranes and of teeth. Compositions which harden to give a rubbery-elastic consistency are preferably used for this purpose.

Rubbery-elastic products can be prepared in various manners. In addition to the polymerisation of unsaturated hydrocarbons containing one or more double bonds, the hardening of thioplasts, for example, which can be effected by reacting aqueous solutions of alkali metal polysulphides with aliphatic dihalides, leads to products with rubbery-elastic properties. Further rubber-like products are formed by the polycondensation of silicones. A further group of rubbery-elastic products is obtained by the polyaddition reaction of a polyester or polyether with a diisocyanate.

The Thiokols have an unpleasant odour before and after the crosslinking. Polyurethanes are physiologically unacceptable since they contain free isocyanate groups. Furthermore, all these compositions exhibit a realtively high polymerisation shrinkage and attempts are made to compensate this by using high proportions of fillers.

In addition, it is customary to prepare rubbery-elastic rubber-like compositions based on ethyleneimine. These products are indeed distinguished by a relatively low polymerisation shrinkage, but have the following disadvantages: when stored in water marked changes in volume occur through swelling processes. Furthermore, the products are physiologically unacceptable since they are crosslinked by aziridine terminal groups. In addition, some aziridines are known to be carcinogenic substances.

All impression materials used in dentistry have limitations from the point of view of time, with respect to both their processing time and their hardening time. After formulation of the reactive mixture, a processing time of about 3 minutes is usually available; as a rule the subsequent hardening time amounts to about 5 minutes.

It has now been found, surprisingly, that polyurethane resins containing vinyl groups can be hardened in the cold to give elastic rubber-like compositions within these times required in practice, and that when used as impression materials, these compositions do not have the abovementioned disadvantages.

The invention thus relates to the use of reaction products of (a) diisocyanates or triisocyanates (preferably diisocyanates (b) dihydroxy compounds having a molecular weight between 300 and 10,000, preferably 1,000 and 8,000, and (c) unsaturated monohydroxy compounds, preferably derivatives of acrylic and/or methacrylic acid which carry hydroxyl groups, which are converted into the crosslinked state during the impression process, as impression materials, in particular for dentistry.

Re (a): The following may be mentioned as diisocyanates or triisocyanates which can be used according to the invention: ethylene-diisocyanate, hexamethylene-diisocyanate, cyclohexane-1,4-diisocyanate, toluylene-2,4- and -2,6-diisocyanate and mixtures thereof, isophorone-diisocyanate, phorone-diisocyanate, naphthaline-1,5-diisocyanate, cyclopentylene-1,3-diisocyanate, m- and p-phenylene-diisocyanate, toluylene-2,4,6-triisocyanate, triphenylmethane-4,4',4''-triisocyanate, xylylene-1,3- and -1,4-diisocyanate, 3,3'-dimethyldiphenylmethane-4,4'-diisocyanate, di-phenyl-methane-4,4'-diisocyanate, dimethylbiphenylene-3,3'-diisocyanate, bisphenylene-4,4'-diisocyanate, durene-diosocyanate, 1-phenoxy-phenylene-2,4'-diisocyanate, 1-tert.-butyl-phenylene-2,4-diisocyanate, methyl-bis-cyclohexyl-4,4'-diisocyanate, 1-chloro-phenylene-2,4-diisocyanate and di-phenyl ether-4,4'-diisocyanate. The di- or tri-isocyanates useful in the invention are preferably hydrocarbon except for the isocyanate groups. However, the hydrocarbon portion can be substituted, for example, by halogen (preferably chlorine), alkoxy of 1-4 carbon atoms or phenoxy.

Furthermore, it is possible to use higher-molecular and optionally also higher-functional polyisocyanates which are prepared from low molecular parent substances by a polymerisation reaction to give uret-diones or isocyanurate derivatives. Examples which may be mentioned are the uret-dione from 2 mols of toluylene-2,4-diisocyanate, and the polymerisation products, containing an isocyanurate ring, from toluylene-2,4- and -2,6-diisocyanate or hexamethylene-diisocyanate, a system which contains, on average, 2 isocyanarate rings in the molecule and which is formed from 5 mols of toluylene-diisocyanate, or a corresponding derivative from, on average, 2 mols of toluylene-diisocyanate and 3 mols of hexamethylene-diisocyanate.

In addition, it is possible to prepare higher urea-linked or biuret-linked systems from diisocyanates or polyisocyanates by partial hydrolysis, via the carbamic acid and amine stage, such as, for example, a biuret-linked compound which is formally obtained from 3 mols of hexamethylene-diisocyanate, 1 mol of water being added and 1 mol of carbon dioxide being split off.

Substances which contain isocyanate groups and which are also suitable are obtained by reacting diols or polyols with difunctional or polyfunctional isocyanates if the molar ratio of hydroxy compound to isocyanate is chosen so that free NCO groups are always present in the statistically formed reaction products and the molecular weight of the reaction products does not exceed 2,000 to 3,000.

Particularly preferred isocyanate-containing compounds which can be used in the resins according to the invention are hexamethylene-diisocyanate, toluylene-diisocyanate, isophorone-diisocyanate and diphenylmethane-4,4'-diisocyanate.

Re (b): Further components which are used for the impression compositions according to the invention are compounds which contain two hydrogen atoms which are reactive towards isocyanates and which have a molecular weight of 300 to 10,000, but preferably of 1,000 to 8,000.

By these compounds there are preferably understood, in addition to compounds containing amino groups, thiol groups or carboxyl groups, polyhydroxy compounds, in particular compounds containing two to eight hydroxyl groups, especially those having a molecular weight of 300 to 10,000, preferably 1,000 to 8,000, for example polyesters, polyethers, polythioethers, polyacetals, polycarbonates and polyester-amides containing, as a rule, two hydroxyl groups, such as are known for the preparation of homogeneous polyurethanes and of cellular polyurethanes.

Possible polyesters containing hydroxyl groups are, for example, reaction products of polyhydric, preferably dihydric and optionally additionally trihydric, alcohols with polybasic, preferably dibasic, carboxylic acids. Instead of the free polycarboxylic acids, it is also possible to use the corresponding polycarboxylic acid anhydrides or corresponding polycarboxylic acid esters of lower alcohols or their mixtures for the preparation of the polyesters. The polycarboxylic acids can be of an aliphatic, cycloaliphatic, aromatic and/or heterocyclic nature and can be optionally substituted, for example by halogen atoms, and/or unsaturated.

Examples which may be mentioned are: succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids, such as oleic acid, optionally mixed with monomeric fatty acids, terephthalic acid dimethyl ester and terephthalic acid bisglycol ester. Possible polyhydric alcohols are, for example, ethylene glycol, propylene 1,2-glycol and 1,3-glycol, butylene 1,4-glycol and 2,3-glycol, hexane-1,6-diol, octane-1,8-diol, neopentylglycol cyclohexanedimethanol (1,4-bis-hydroxymethylcyclohexane), 2-methylpropane-1,3-diol, glycerol, trimethylolpropane, hexane-1,2,6-triol, butane-1,2,4-triol, trimethylolethane, pentaerythritol, quinitol, mannitol and sorbitol, methylglycoside and furthermore diethylene glycol, triethylene glycol, tetraethylene glycol, polyethylene glycols, dipropylene glycol, polypropylene glycols, dibutylene glycol and polybutylene glycols. The polyesters can contain a proportion of terminal carboxyl groups. Polyesters from lactones, for example ε-caprolactone, or hydroxycarboxylic acids, for example ε-hydroxycaproic acid, can also be used.

The polyethers which contain, as a rule, two hydroxyl groups and which are possible according to the invention are also those of the type which is in itself known, and are prepared, for example, by polymerisation of epoxides, such as ethylene oxide, propylene oxide, butylene oxide, tetrahydrofurane, styrene oxide or epichlorohydrin, with themselves, for example in the presence of BF$_3$, or by addition of these epoxides, optionally as a mixture or successively, to starting components containing reactive hydrogen atoms, such as water, alcohols, ammonia or amines, for example ethylene glycol, propylene 1,3-glycol or 1,2-glycol, 4,4'-dihydroxy-diphenylpropane, aniline and ethanolamine. In many cases, those polyethers which predominantly contain (up to 90% by weight, relative to all the OH groups present in the polyether) primary OH groups are preferred. Polyethers modified by vinyl polymers, such as are formed, for example, by the polymerisation of styrene and acrylonitrile in the presence of polyethers [U.S. Pat. Nos. 3,383,351, 3,304,273, 3,523,093 and 3,110,695 and German Patent Specification 1,152,536], are also suitable, as are polybutadienes containing OH groups.

Polythioethers which may be mentioned are, in particular, the condensation products of thiodiglycol with itself and/or with other glycols, dicarboxylic acids, formaldehyde, aminocarboxylic acid or aminoalcohols. Depending on the CO components, the products are mixed polythioethers, polythioether-esters or polythioether-ester-amides.

Possible polyacetals are, for example, the compounds which can be prepared from glycols, such as diethylene glycol, triethylene glycol, 4,4'-dihydroxyethoxydiphenyldimethylmethane and hexanediol, and formaldehyde. Polyacetals which are suitable according to the invention can also be prepared by polymerisation of cyclic acetals.

Possible polycarbonates containing hydroxyl groups are those of the type which is in itself known, which can be prepared, for example, by reacting diols, such as propane-1,3-diol, butane-1,4-diol and/or hexane-1,6-diol, diethylene glycol, triethylene glycol or tetraethylene glycol, with diaryl carbonates, for example diphenyl carbonate, or phosgene.

The polyester-amides annd polyamides include, for example, which are obtained from polybasic saturated and unsaturated carboxylic acids or their anhydrides and polyhydric saturated and unsaturated aminoalcohols, diamines, polyamines and their mixtures, predominantly linear condensation products.

Polyhydroxy compounds which already contain urethane groups or urea groups as well as optionally modified naturally occurring polyols, such as castor oil, carbohydrates or starches, can also be used. According to experience, it is also possible to employ addition products of alkylene oxides and phenol/formaldehyde resins or urea/formaldehyde resins.

Mixtures of the abovementioned compounds which contain, as a rule, two isocyanates reactive hydrogen atoms and which have a molecular weight of 300–10,000, for example mixtures of polyethers and polyesters, can, of course, be used.

Re (c): Vinyl compounds which are capable of polymerisation and which contain a hydrogen which is reactive towards isocyanates are used as the third component of the compositions according to the invention. Hydroxyalkylation products of acrylic and/or methacrylic acid are preferably employed, such as acrylic acid hydroxyethyl ester, acrylic acid hydroxypropyl ester, methacrylic acid hydroxyethyl ester and methacrylic acid hydroxypropyl ester.

The three components from which the polyurethane compositions, according to the invention, containing vinyl groups are built up, namely diisocyanates, dihydroxy compounds and hydroxyalkyl esters of acrylic and/or methacrylic acid, are preferably reacted with one another in the following stoichiometric proportions: 2 mols of diisocyanate and 2 mols of the hydroxyalkyl ester of acrylic and/or methacrylic acid are used per 1 mol of the dihydroxy compound. However, deviations from this rule are quite possible: in particular, several molecules of the dihydroxy compound can be first lengthened by reaction with diisocyanates before their ends are reacted with the hydroxyalkyl ester of acrylic and/or methacrylic acid.

The polyurethane compositions, used according to the invention, containing vinyl groups are appropriately prepared in the presence of catalysts which are in themselves known. Examples of possible catalysts are: tertiary amines, such as triethylamine, tributylamine, N-methyl-morpholine, N-ethylmorpholine, N-coconut alkyl-morpholine, N,N,N'-tetramethylethylenediamine, 1,4-diaza-bicyclo-(2,2,2)-octane, N-methyl-N'-dimethylamino-ethyl-piperazine, N,N-dimethylbenzylamine, bis-(N,N-diethylaminoethyl) adipate, N,N-diethylbenzylamine, pentamethyldiethylenetriamine, N,N-dimethylcyclohexylamine, N,N,N',N'-tetramethyl-1,3-butanediamine, N,N-dimethyl-β-phenylethylamine, 1,2- dimethylimidazole, and 2-methylimidazole. Mannich bases, which are in themselves known, obtained from secondary amines, such as dimethylamine, and aldehydes, preferably formaldehyde, or ketones, such as acetone, methyl ethyl ketone or cyclohexanone, and phenols, such as phenol, nonylphenol and bisphenol, can also be used as catalysts.

Examples of tertiary amines which contain hydrogen atoms which are active towards isocyanate groups and which can be used as the catalysts are triethanolamine, triisopropanolamine, N-methyldiethanolamine, N-ethyldiethanolamine and N,N-dimethylethanolamine, as well as their reaction products with alkylene oxides, such as propylene oxide and/or ethylene oxide.

Furthermore, sila-amines containing carbon-silicon bonds, such as are described, for example, in German Patent Specification No. 1,229,290 [corresponding to U.S. Pat. No. 3,620,984], for example 2,2,4-trimethyl-2-silamorpholine and 1,3-diethylaminomethyltetramethyl-disiloxane, are also possible catalysts.

It is also possible to use nitrogen-containing bases, such as tetraalkylammonium hydroxides, and furthermore alkali metal hydroxides, such as sodium hydroxide, alkali metal phenolates, such as sodium phenolate, or alkali metal alcoholates, such as sodium methylate, as the catalysts. Hexahydrotriazines can also be employed as the catalysts.

Furthermore, organic metal compounds, in particular organic tin compounds, can also be used as the catalysts.

Preferred possible organic tin compounds are tin-II salts of carboxylic acids (particularly alkane carboxylic acids), such as tin-II acetate, tin-II octoate, tin-II ethylhexoate and tin-II laurate, and tin-IV compounds, for example dialkyl of 4 to 8 carbon atom tin compounds, such as dibutyl-tin oxide, dibutyl-tin dichloride, dibutyl-tin diacetate, dibutyl-tin dilaurate, dibutyl-tin maleate or dioctyl-tin diacetate. It is possible, of course, to employ all the abovementioned catalysts in the form of mixtures.

Further representatives of suitable catalysts and details on the mode of action of the catalysts are described in Kunststoff-Handbuch (Plastics Handbook), volume VII, edited by Vieweg and Höchtlen Carl-Hanser-Verlag, Munich, 1966, for example on pages 96 to 102.

As a rule, the catalysts are employed in an amount of between about 0.001 and 10% by weight, relative to the total amount.

In the preparation of the compositions used according to the invention, it is possible to mix the dihydroxy compound with the hydroxyalkyl ester of acrylic and/or methacrylic acid and to react the mixture with the diisocyanate subsequently introduced. However, as a rule a reaction procedure in which equimolar amounts of the unsaturated hydroxyalkyl ester and of the diisocyanate are first reacted with one another, after which this precondensate is reacted with the dihydroxy compound in a subsequent reaction, is recommended. In principle, however, the procedure depends on the properties which the unsaturated urethane composition should have.

In order to avoid premature gelling of these compositions and to guarantee their stability to storage, it is appropriate to already add one or more polymerisation inhibitors during the preparation. Examples of suitable auxiliaries of this type, which can be added in amounts of 0.001 to 0.1% by weight, relative to the total mixture, are phenols and phenol derivatives, preferably sterically hindered phenols, which contain, in both o- positions relative to the phenolic hydroxyl group, alkyl substituents with 1-6 C atoms, amines, preferably secondary arylamines and their derivatives, quinones, copper-I salts of organic acids or addition compounds of copper-I halides and phosphites, but also phosphites by themselves.

There may be mentioned, by name: 4,4'-bis-(2,6-di-tert.-butylphenol), 1,3,5-trimethyl-2,4,6-tris-(3,5-di-tert.-butyl-4-hydroxy-benzyl)-benzene, 4,4'-butylidene-bis-(6-tert.-butyl-m-cresol), 3,5-di-tert.-butyl-4-hydroxybenzyl-phosphonic acid diethyl ester, N,N'-bis-(β-naphthyl)-p-phenylene-diamine, N,N'-bis-(1-methylheptyl)-p-phenylenediamine, phenyl-β-naphthylamine, 4,4'-bis-(α,α-dimethylbenzyl)-diphenylamine, 1,3,5-tris-(3,5-di-tert.-butyl-4-hydroxy-hydrocinnamoyl)-hexahydro-s-triazine, hydroquinone, p-benzoquinone, 2,5-di-tert.-butylquinone, toluhydroquinone, p-tert.-butyl-pyrocatechol, 3-methylpyrocatechol, 4-ethylpyrocatechol, chloranil, naphthoquinone, copper naphthenate, copper octoate, Cu-I Cl/triphenyl phosphite, Cu-I Cl/trimethyl phosphite, Cu-I Cl/trischloroethyl phosphite, Cu-I Cl/tripropyl phosphite, p-nitrosodimethylaniline and triethyl phosphite.

Further suitable stabilisers are described in "Methoden der organischen Chemie" ("Methods of Organic Chemistry") (Houben-Weyl), 4th edition, volume XIV/1, page 433–452 and 756, Georg Thieme Verlag, Stuttgart, 1961.

Phenothiazine is also a very suitable stabiliser.

The phases, to be used according to the invention, prepared from the abovementioned components in the manner described are intended for use as an impression material in dentistry. They prove particularly suitable for this intended use since no polymerisation shrinkage at all, or only an extremely slight polymerisation shrinkage, can be observed during their hardening to give rubber-like shaped articles.

The compositions used according to the invention are hardened using the customary hardening catalysts such as are used, for example, for hardening so-called unsaturated polyester resins. Suitable polymerisation initiators are peroxides, optionally in the presence of accelerators such as aromatic amines or cobalt compounds. Whilst hardening at elevated temperature can be carried out by means of peroxides alone or free radical initiators, such as, for example, azoisobutyric acid dinitrile, hardening at room temperature requires the addition of accelerators, preferably aromatic amines. A typical hardening when polyurethane compositions containing vinyl groups are used according to the invention can be carried out, for example, with the addition of 1% by weight of benzoyl and 1% by weight of N,N-dimethylaniline.

Hardening by means of high-energy rays, such as electron rays or gamma rays or, if photo-initiators are added to the resin, by means of UV light is also possible. Examples of suitable photo-initiators are benzophenone and its derivatives, benzoin and its derivatives, such as benzoin ether, anthraquinones and aromatic disulphides.

Particular viscosity characteristics are a prerequisite of the use according to the invention of the polyurethane compositions in dental practice. These characteristics must be of a nature such that practical application is possible. Such desired viscosity characteristics can be essentially achieved by means of the stoichiometry and reactants in the synthesis of the unsaturated urethane resins. It is also possible to influence the desired processing consistency by matching the diluents and fillers in the desired manner. Examples of diluents which may be mentioned are: inert organic solvents, such as, for example, hydrocarbons, toluene and xylene, furthermore ethers, such as diethyl ether, and ethylene glycols, but also liquid polyethers and alcohols, such as ethanol, butanol, octanol, glycol or glycerol. Particularly preferred diluents are so-called plasticisers, such as are used, for example, in the processing of polyvinyl chloride. Examples of compounds which can be used here are esters of phthalic acid or esters of adipic acid, as well as esters of phosphoric acid. Phenyl esters of alkanesulphonates are also suitable.

In special cases it can be advisable to use copolymerisable vinyl monomers as the diluent. For example, esters of acrylic acid, esters of methacrylic acid, styrene and vinyl acetate can be added. Preferred esters of acrylic acid are acrylic acid isooctyl ester, acrylic acid dodecyl ester, hexane-1,6-diol diarylate, trimethylolpropane triacrylate, ethylene glycol diacrylate and the corresponding esters of methacrylic acid.

Further formulation auxiliaries which may be mentioned are: animal and vegetable fats, such as cotton seed oil, groundnut oil, maize germ oil, olive oil, castor oil and sesame oil, and furthermore waxes, paraffin, polyethylene glycols, silicones and the like.

The fillers can be reinforcing and/or non-reinforcing fillers. Reinforcing fillers are understood as those fillers which have a surface area of at least 50 m$^2$/g. Examples which may be mentioned are: pyrogenically produced silicon dioxide, silicon dioxide aerogels, calcium silicate, diatomaceous earth and titanium dioxide. Non-reinforcing fillers which may be mentioned are: quartz powder, sea sand, zirconium silicate, aluminium silicate, aluminium hydroxide, aluminium oxide, zinc oxide, gypsum, limestone, dolomite, overburned gypsum and chalk, but also fillers of an organic origin, such as starches and plastics powders, such as, for example, polyethylene powder, PVC powder and polyamide powder.

Mixtures of various fillers can also be used. The fillers are preferably employed in amounts of 1–90% by weight, in particular of 5–80% by weight, relative to the total weight of the particular base material.

Non-reinforcing fillers are preferably employed in amounts of more than 10% by weight of the total composition.

Reinforcing fillers are preferably employed in amounts of 1–10% by weight of the particular impression composition. However, it is also possible to employ larger amounts of reinforcing fillers as long as the homogeneity of the compositions does not suffer as a result.

The impression compositions according to the invention can also contain odour-improving and flavour-improving additives, for example peppermint oil or eucalyptus oil, and sweeteners, for example saccharin. They can be coloured both with soluble organic dyestuffs and with organic or inorganic pigments.

In contrast to all the other products which were hitherto customary for impression materials, the material to be used according to the invention is distinguished by particular hardness characteristics. In contrast to, for example, polyethers and Thiokols, the viscosity of which already rises slowly immediately after the addition of the hardening components, the material to be used according to the invention changes only slightly during the processing time range determined by dentistry, and whilst, for example, polyethers and Thiokols only achieve their final Shore hardness values after about 30 minutes, in the case of the material to be used according to the invention the final Shore hardness is already obtained immediately after the end of hardening, that is to say in a substantially shorter time, namely after about 4–5 minutes. It should also be mentioned that, in contrast to Thiokols and polyethers, a high desirable degree of Shore hardness is already achieved with very small proportions of fillers in the composition described according to the invention. The special properties of the impression compositions according to the invention can be varied greatly by choosing suitable starting materials, so that the mechanical properties and the processing properties can be adjusted to all applications of impression materials.

Compared with the rubbery-elastic impression compositions used hitherto, for example those based on Thiokols, the material to be used according to the invention have the considerable advantage of being odourless. The very good adhesion or ability of the products according to the invention to stick, in particular to metals and plastics, there being materials which are used for the preparation of impression spoons, is also to be singled out.

The finished impression materials can be packed either as pre-proportioned units or in larger amounts. The peroxidic hardener can be added either in the liquid, solid or paste-like form, it being possible, in the case of paste-like hardeners, to use all the abovementioned auxiliaries and fillers which are stable towards peroxides. The hardener paste preferably has a similar consistency to the impression paste, and the hardener is preferably measured out in the same ribbon length as the stock paste.

The new polyurethane resins, according to the invention, containing vinyl groups are preferably used in the field of dentistry. However, it goes without saying that their use is not restricted to this field; rather, they can be used in all cases where a precise impression of contours is required. The moulds obtainable in this way can be filled in the generally customary manner with gypsum or other casting materials in order to obtain a positive copy of the original object from which the impression was taken.

The preparation and use according to the invention of the polyurethane resins, according to the invention, containing vinyl groups is illustrated in more detail in the examples which follow.

EXAMPLE 1

581 g of hexamethylene-diisocyanate are initially introduced into a 2 l round-bottomed flask, with a dropping funnel, stirrer and a device for introducing air, and a mixture consisting of 504 g of hydroxypropylmethacrylate, 1.12 g of phenothiazine and 5.3 g of a tin octoate solution (Desmorapid SO, Bayer AG) is added slowly at 60° C., whilst passing air through. After the exothermic reaction has subsided, this condensation product is stirred, at 60° C. and while passing air through, into 4,559 g of a linear polyester obtained from adipic acid and diethylene glycol (MW=2,100, hydroxyl number=40±5). After a reaction time of 10 hours at 60° C., the content of NCO groups which could be analytically determined was 0.14%. After cooling the reaction product, a viscous resin resulted.

EXAMPLE 2

Hydroxypropylmethacrylate, the polyester obtained from adipic acid and diethylene glycol, phenothiazine and tin octoate are mixed in the same stoichiometric combination as in Example 1, and the mixture is reacted with hexamethylenediisocyanate at 60° C., whilst passing air through. After a reaction time of 15 hours, a resin which is highly viscous at room temperature and in which 0.34% of free NCO groups could still be detected analytically results.

EXAMPLE 3

432 g of hydroxypropylmethacrylate, 1.7 g of phenothiazine, 5 g of tin octoate solution, 485 g of hexamethylenediisocyanate and 5,880 g of a linear polyester obtained from adipic acid, butanediol and ethylene glycol (MW=4,000, hydroxyl number=28.6) are reacted analogously to Example 1. After a reaction time of 10 hours, a highly viscous resin with a content of free isocyanate groups of 0.05% results.

EXAMPLE 4

116 g of acrylic acid hydroxyethyl ester, 0.06 g of p-methoxyphenol, 1.0 g of triethylamine, 168 g of hexamethylenediisocyanate and 1,000 g of a linear polypropylene oxide (MW=2,000±100, hydroxy number=56±3) are reacted according to Example 2. A mobile resin with a viscosity of 2,400 cP results.

EXAMPLE 5

852 g of toluylene-2,4-diisocyanate, 720 g of hydroxypropylmethacrylate, 0.3 g of p-methoxyphenol, 4 g of tin octoate solution and 6,252 g of a polyester obtained from adipic acid and diethylene glycol (MW=2,100, hydroxyl number=40±5) are reacted analogously to Example 1. After a reaction time of 12 hours at 60° C., a highly viscous resin in which free NCO groups can no longer be detected analytically results.

EXAMPLE 6

220 g of isophorone-diisocyanate, 144 g of hydroxypropylmethacrylate, 0.33 g of phenothiazine and 1,302 g of a polyester obtained from adipic acid and diethylene glycol (MW=2,100, hydroxy number=40±5) are reacted according to Example 1. After 24 hours at 60° C., a highly viscous resin with a content of free NCO groups of 0.51% results.

EXAMPLE 7

60 parts by weight of the resin described in Example 1 are mixed in a kneader with 20 parts by weight of talc, 4 parts by weight of calcium silicate, 15.9 parts by weight of a linear polyester having a molecular weight of 2,000 and 0.1 part by weight of p-dimethyltoluidine for 1 hour.

10 parts by weight of the paste described above are mixed vigorously with 0.2 part by weight of a paste consisting of 50% by weight of dibenzoyl peroxide and 50% by weight of dibutyl phthalate for 30 seconds. Hardening is complete after about 4 minutes. Measurement of the linear shrinkage gives the following values:
15': −0.013%
30': −0.007%
1 hour: +0.020%
6 hours: +0.033%
24 hours: +0.018%

EXAMPLE 8

54 parts by weight of the resin described in Example 2 are mixed in a kneader with 37.8 parts by weight of talc, 8.1 parts by weight of dioctyl phthalate and 0.1 part by weight of p-dimethylxylidone for 1 hour.

10 parts by weight of the paste described above are mixed with 2 parts by weight of a paste consisting of 4 parts by weight of 50% strength dibenzoyl peroxide in dibutyl phthalate, 61 parts by weight of talc and 35 parts by weight of dibutyl phthalate. The following Shore hardnesses were measured:
4' 30": 58
6': 60
8': 60
10': 61

After 2 hours 30', the shrinkage value, measured linearly, was 0.0294%.

EXAMPLE 9

44 parts by weight of the resin described in Example 3 are mixed in a kneader with 12 parts by weight of an alkylsulphonic acid phenyl ester (Mesamoll® from Bayer AG), 12 parts by weight of a linear polyester having a molecular weight of 400, 22 parts by weight of talc, 5 parts by weight of polypropylene powder and 0.1 part by weight of dimethylaniline for 2 hours.

10 parts by weight of the paste described above are mixed with 4 parts by weight of a paste consisting of 4 parts by weight of 50% strength dichlorobenzoyl peroxide in dibutyl phthalate, 60 parts by weight of annaline (overburned gypsum) and 36 parts by weight of an alkylsulphonic acid phenyl ester (Mesamoll® from Bayer AG). The following linear shrinkage values were found:
15': −0.037%
30': −0.060%
1 hour: −0.075%
3 hours: −0.117%
6 hours: −0.126%
24 hours: −0.212%

EXAMPLE 10

33.3 parts by weight of the resin prepared in Example 3 and 7.4 parts by weight of the resin prepared in Example 1, as well as 9.3 parts by weight of an alkylsulphonic acid phenyl ester (Mesamoll® from Bayer AG), 18.5 parts by weight of a linear polyester having a molecular weight of 2,000, 18.5 parts by weight of talc, 12.9 parts by weight of polyethylene powder and 0.1 part by weight of p-dimethyltoluidine are mixed in a kneader for 4 hours.

10 parts by weight of the paste described above are mixed with 2 parts by weight of the peroxide paste described in Example 8. The following values of the linear shrinkage were found:
15': −0.013%
30': −0.007%
1 hour: ±0%
4 hours: +0.009%
24 hours: −0.004%

A value of 1.11% was found for the residual deformation and a value of 5.68% was found for the elastic deformation.

What is claimed is:
1. An impression material for use in dentistry comprising (I) the reaction product of (a) a diisocyanate or triisocyanate, (b) a dihydroxy compound selected from the group consisting of polyesters, polyethers, polythioethers, polyacetals, polycarbonates and polyesteramides having a molecular weight of from 300 to 10,000 and (c) a derivative of acrylic and/or methacrylic acid having a hydroxyl group wherein the molar ratio of compounds (a), (b) and (c) is 2:1:2, and (II) an inert dental carrier, said impression material having a hardening time of about 4–5 minutes.

2. A material according to claim 1 wherein the isocyanate (a) is a diisocyanate.

3. A material according to claim 2 wherein the diisocyanate (a) is hexamethylene-diisocyanate, toluylene-diisocyanate, isophorone-diisocyanate or diphenylmethane-4,4'-diisocyanate.

4. A material according to claim 2 wherein the dihydroxy compound (b) has a molecular weight of from 1,000 to 8,000.

5. A process for preparing an impression material according to claim 1 which comprises mixing the dihydroxy compound (b) with the monohydroxy compound (c), then reacting the mixture with the diisocyanate (a).

6. A process for preparing an impression material according to claim 1 which comprises reacting equimolar amounts of compounds (a) and (c), then reacting the reaction product with compound (b).

7. A process according to claim 5 wherein a polymerization inhibitor is present to prevent premature gelling.

8. A process according to claim 6 wherein a polymerization inhibitor is present to prevent premature gelling.

9. An impression material according to claim 1 additionally containing a hardening catalyst.

10. A material according to claim 1 wherein the dihydroxy compound (b) has a molecular weight of from 2,000 to 4,000.

11. A material according to claim 2 wherein the dihydroxy compound (b) has a molecular weight of from 2,000 to 4,000.

* * * * *